United States Patent
Peng (10) Patent No.: US 10,751,487 B2
(45) Date of Patent: Aug. 25, 2020

(54) NEBULIZER WITH PRESS-TYPE MEDICINE CUP

(71) Applicant: Delta Electronics, Inc., Taoyuan (TW)

(72) Inventor: Wan-Chen Peng, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 450 days.

(21) Appl. No.: 15/846,997

(22) Filed: Dec. 19, 2017

(65) Prior Publication Data

US 2018/0361084 A1 Dec. 20, 2018

(30) Foreign Application Priority Data

Jun. 20, 2017 (CN) .......................... 2017 1 0470810

(51) Int. Cl.
*A61M 11/00* (2006.01)
*B65D 43/12* (2006.01)
*B65D 41/02* (2006.01)

(52) U.S. Cl.
CPC ........... *A61M 11/005* (2013.01); *A61M 11/00* (2013.01); *A61M 11/002* (2014.02);
(Continued)

(58) Field of Classification Search
CPC ................ A61M 11/005; A61M 11/00; A61M 2205/8206; A61M 11/002; A61M 11/02; A61M 2205/12; A61M 11/001; A61M 11/041; A61M 11/042; A61M 11/06; A61M 11/08; A61M 15/00; A61M 15/0013; A61M 15/0016; A61M 15/002; A61M 15/0021; A61M 15/0028; A61M 15/0068; A61M 15/0076; A61M 15/0081; A61M 15/0085; A61M 15/0086; A61M 15/009; A61M 15/06; A61M 16/0808; A61M 16/0816;
(Continued)

(56) References Cited

U.S. PATENT DOCUMENTS

2010/0096408 A1* 4/2010 Schiewe ............. B05B 11/0054 222/83
2013/0144215 A1* 6/2013 Esteve ................ B05B 11/3057 604/151

(Continued)

*Primary Examiner* — Samchuan C Yao
*Assistant Examiner* — Rachel H. Moon
(74) *Attorney, Agent, or Firm* — Chun-Ming Shih; HDLS IPR Services (57) ABSTRACT

A nebulizer with a press-type medicine cup is provided. The nebulizer includes a body, a medicine cup, an engagement structure, and a multi-directional resilient member. The engagement structure includes an inner protruding base and an outer protruding block disposed outside the inner protruding base. The inner protruding base and the outer protruding block extend from the body and the medicine cup. The inner protruding base includes a cavity inside and includes two through holes. The outer protruding block includes two engagement grooves. The multi-directional resilient member is installed in the cavity and includes a press element, two straight resilient arms extend from the press element, two oblique resilient arms are bent from the two straight resilient arms, and each oblique resilient arm has a block member. The two block members are inserted through the two through holes to be engaged with the two engagement grooves.

11 Claims, 10 Drawing Sheets

(52) U.S. Cl.
CPC ... *A61M 2205/8206* (2013.01); *B65D 41/026* (2013.01); *B65D 43/12* (2013.01)

(58) Field of Classification Search
CPC .......... A61M 16/0833; A61M 16/1075; A61M 16/16; A61M 2016/0021; A61M 2202/0208; A61M 2202/064; A61M 2205/11; A61M 2205/3553; A61M 2205/3569; A61M 2205/3584; A61M 2205/3592; A61M 2205/3606; A61M 2205/3653; A61M 2205/52; A61M 2205/581; A61M 2205/583; A61M 2205/587; A61M 2205/7536; A61M 2205/8237; A61M 2209/082; A61M 2230/06; A61M 2230/201; A61M 2230/40; A24F 40/00; A24F 40/44; A24F 47/002; A24F 47/008; A61K 31/465; B05B 11/0054; B05B 11/02; B05B 11/3091; B65D 41/026; B65D 41/26; B65D 41/265; B65D 43/12; B65D 43/26; F16M 11/041; F16M 2200/025; F16B 7/042; F16B 7/0473

See application file for complete search history.

(56) References Cited

U.S. PATENT DOCUMENTS

2016/0361506 A1* 12/2016 Lin ................... H02J 7/0063
2018/0065160 A1*  3/2018 Cheng ................ B05B 15/55

* cited by examiner

NEBULIZER WITH PRESS-TYPE MEDICINE CUP

TECHNICAL FIELD

The present invention relates to a nebulizer structure and, in particular, to a nebulizer with a press-type medicine cup.

BACKGROUND

Due to development of medical technology, medical nebulizers are available to allow patients to take medicine effectively and conveniently. The nebulizer turns a medicinal liquid into medicinal aerosol and then delivers, via a passage or a port, the medicinal aerosol into the patient's mouth, thus providing treatment rapidly and effectively. Therefore, the nebulizers have been widely adopted nowadays.

Conventional nebulizers typically include ultrasonic nebulizers and pneumatic (compressed gas) nebulizers. The ultrasonic nebulizers utilize ultrasonic sound waves to turn the medicinal liquid into the aerosol. In the pneumatic medical nebulizers, a compressed gas passes through a small tube opening to generate a high-speed airflow, which causes a negative pressure. By means of the negative pressure, the liquid and/or other fluid are jetted to an obstruction object and impact it at high speed, and then the medicinal liquid is spattered to transform liquid drops into a fine spray to be discharged from a tube.

No matter it is an ultrasonic nebulizer or a pneumatic nebulizer, the medicine cup can be replaced by pushing. However, for the conventional nebulizer with a medicine cup changed by pushing, multiple springs are required to be installed inside in order to achieve bidirectional movement. Therefore, the conventional nebulizer has complicated components and requires high production costs. Industries desire to provide an improved nebulizer with simplified components and reduced springs.

In views of this, in order to solve the above disadvantages, the present inventor studied related technology and provided a reasonable and effective solution in the present disclosure.

SUMMARY

The present invention provides a nebulizer with a press-type medicine cup. The medicine cup can be replaced by pushing a multi-directional resilient member. The nebulizer eliminates the need for multiple springs which are otherwise needed by a conventional nebulizer. Therefore, the nebulizer has simplified components and a simple structure for easy assembly and also saves production costs.

In the embodiment of the present invention, the present invention provides a nebulizer with a press-type medicine cup, comprising: a body; a medicine cup; an engagement structure, the engagement structure including an inner protruding base and an outer protruding block disposed outside the inner protruding base, the inner protruding base extending from one of the body and the medicine cup, the outer protruding block extending from the other one of the body and the medicine cup, the inner protruding base including a cavity inside and including an opening and two through holes communicating with the cavity, the outer protruding block including two engagement grooves; and a multi-directional resilient member installed in the cavity, the multi-directional resilient member including a press element, two straight resilient arms extending from the press element, two oblique resilient arms being bent backward from the two straight resilient arms, a block member being disposed at a distal end of each of the oblique resilient arms, the press element being inserted through and exposed from the opening, the two block members being inserted through the two through holes and engaged with the two engagement grooves respectively, wherein when the press element is pressed, the two block members are driven to retract into the two through holes to be released from the two engagement grooves, so that the medicine cup is detachably connected to the body.

Accordingly, when the multi-directional resilient member moves, it causes movement in two directions, i.e. the press member is exposed from or retracts into the opening, and the block member is exposed from or retracts into the through holes. Therefore, the nebulizer can use a single multi-directional resilient member, instead of multiple springs, while achieving bi-directional movement to facilitate resilient restoration.

BRIEF DESCRIPTION OF THE DRAWINGS

The disclosure will become more fully understood from the detailed description, and the drawings given herein below is for illustration only, and thus does not limit the disclosure, wherein.

DETAILED DESCRIPTION

Detailed descriptions and technical contents of the present invention are illustrated below in conjunction with the accompany drawings. However, it is to be understood that the descriptions and the accompany drawings disclosed herein are merely illustrative and exemplary and not intended to limit the scope of the present invention.

Please refer to FIGS. 1 to 8 illustrating a nebulizer with a press-type medicine cup according to the first embodiment of the present invention. The nebulizer 10 includes a body 1, a medicine cup 2, an engagement structure 3 and a multi-directional resilient member 4.

As shown in FIG. 1, FIG. 2 and FIGS. 4 to 8, the body 1 is a power supply body 11, i.e. the power supply body 11 including a battery inside for supplying power. The power supply body 11 includes a switch 111 and a plurality of electrodes 112.

As shown in FIG. 1, FIG. 2, and FIGS. 4 to 8, the medicine cup 2 includes a spray hole 21, a medicinal liquid chamber 22 is disposed inside the medicine cup 2, and the medicinal liquid chamber 22 communicates with the spray hole 21. A fine spray generator (not illustrated) is installed inside the medicine cup 2. The medicine cup 2 includes a plurality of conductive portions 23 electrically connected to the fine spray generator. Each electrode 112 is electrically connected to each of the conductive portions 23, so that the power supply body 11 supplies power to the fine spray generator.

The fine spray generator (not illustrated) can be a sound wave oscillating device or a pneumatic device. The sound wave oscillating device utilizes ultrasonic sound waves to turn a medicinal liquid into aerosol and discharge it from the spray opening 21. In the pneumatic device, a compressed gas passes through a small tube opening at high speed, which causes a negative pressure. By means of the negative pressure, the medicinal liquid is jetted to an obstruction object and impacts it at high speed, and then the medicinal liquid is spattered to transform liquid drops into the fine spray to be discharged from the spray opening 21.

As shown in FIG. 1, FIG. 2, and FIGS. 4 to 8, the engagement structure 3 includes an inner protruding base 31 and an outer protruding block 32 disposed outside the inner protruding base 31. The inner protruding base 31 extends from one of the body 1 and the medicine cup 2, the outer protruding block 32 extends from the other one of the body 1 and the medicine cup 2, the inner protruding base 31 includes a cavity 311 inside and includes an opening 312 and two through holes 313 communicating with the cavity 311, and the outer protruding block 32 includes two engagement grooves 321. According to the present embodiment, the inner protruding base 31 integrally extends from the body 1, the outer protruding block 32 extends from the medicine cup 2; however, the present invention is not limited in this regard.

To be specific, the engagement structure 3 further includes two first blockers 33 and two second blockers 34, the two first blockers 33 are formed at respective inner surfaces of the two through holes 313 away from the press element 41, the two second blockers 34 are formed at the respective inner surfaces of the two through holes 313 close to the press element 41, the two first blockers 33 are in contact with the two block members 431 respectively, and the two second blockers 34 are in contact with the two block members 431 respectively. As shown in FIGS. 1 to 4, and FIGS. 6 to 8, the multi-directional resilient member 4 is installed in the cavity 311, the multi-directional resilient member 4 includes a press element 41, two straight resilient arms 42 extend from the press element 41, two oblique resilient arms 43 are bent backward from the two straight resilient arms 42, a block member 431 is disposed at a distal end of each of the oblique resilient arms 43, and each of the oblique resilient arms 43 includes an outer oblique side 432.

When the press element 41 is inserted through and exposed from the opening 312, the two block members 431 are inserted through and exposed from the two through holes 313 respectively, and each of the oblique resilient arms 43 forms a first acute angle $\theta$ with respect to a corresponding one of the straight resilient arms 42.

When the press element 41 is pressed, the two block members 431 are driven to retract into the two through holes 313 to be released from the two engagement grooves 321, so that the medicine cup 2 can be assembled to or be detached from the body 1.

As shown in FIGS. 1 to 8, the nebulizer 10 of the present invention is characterized in that, the engagement structure 3 includes the inner protruding base 31 and the outer protruding block 32 disposed outside the inner protruding base 31, the inner protruding base 31 extends integrally from one of the body 1 and the medicine cup 2, the outer protruding block 32 extends from the other one of the body 1 and the medicine cup 2, the inner protruding base 31 includes the cavity 311 inside and also includes the opening 312 and the two through holes 313 communicating with the cavity 311, and the outer protruding block 32 includes the two engagement grooves 321. Furthermore, the multi-directional resilient member 4 is installed in the cavity 311, the multi-directional resilient member 4 includes the press element 41, the two straight resilient arms 42 extend from the press element 41, the two oblique resilient arms 43 are bent backward from the two straight resilient arms 42, the block member 431 is disposed at the distal end of each of the oblique resilient arms 43, the press element 41 is inserted through and exposed from the opening 312, the two block members 431 are inserted through the two through holes 313 respectively and are engaged with the two engagement grooves 321. When the press element 41 is pressed, the two block members 431 are driven to retract into the two through holes 313 to be released from the two engagement grooves 321, so that the medicine cup 2 is detachably connected to the body 1. Accordingly, the medicine cup 2 can be replaced by a pushing method using the multi-directional resilient member 4. In addition to that, the present invention eliminates the need for multiple springs which would be otherwise needed by a conventional nebulizer. Therefore, the nebulizer 10 has simplified components, is easy to assemble, and saves production costs.

Figure 1:
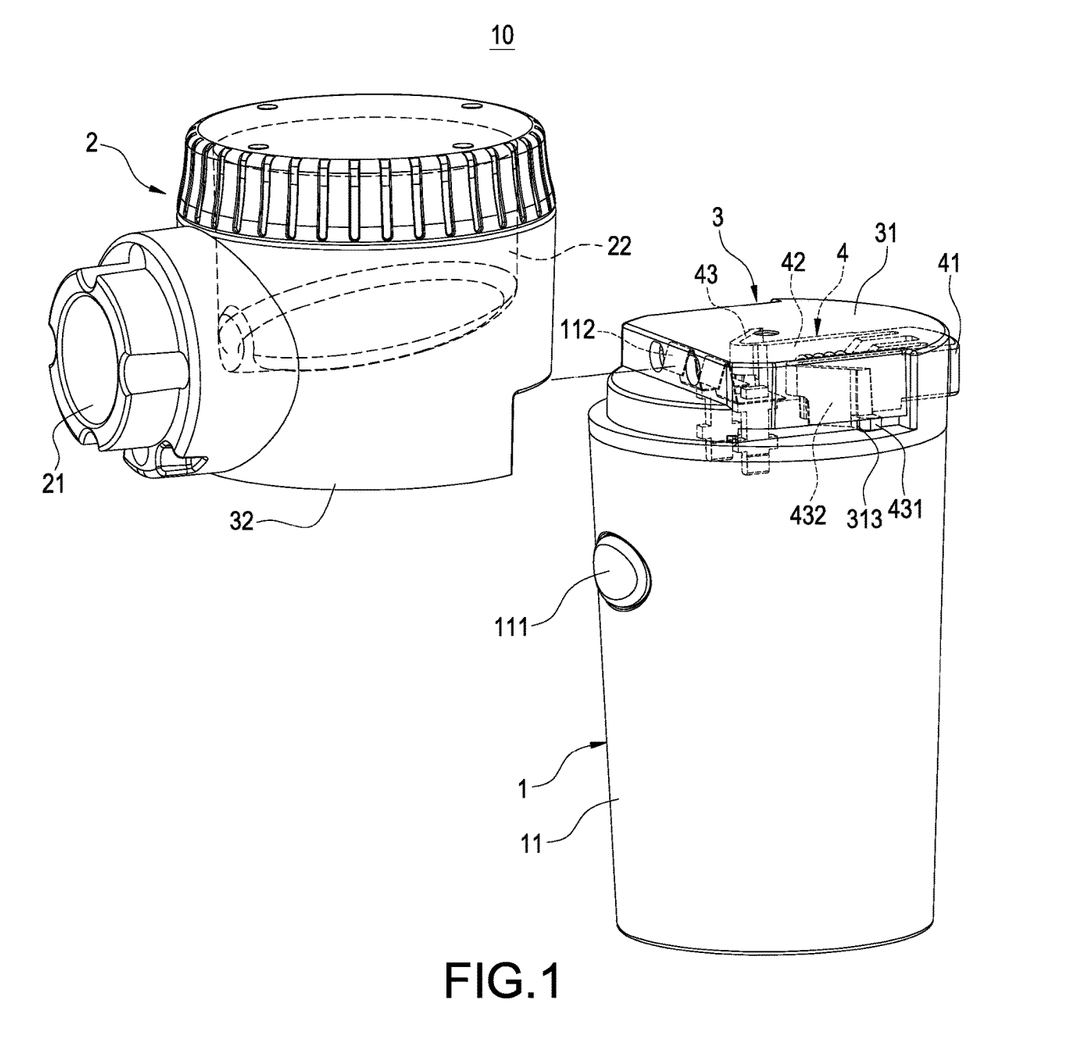
FIG. 1 is a perspective exploded view illustrating a nebulizer according to the first embodiment of the present invention.
Figure 2:
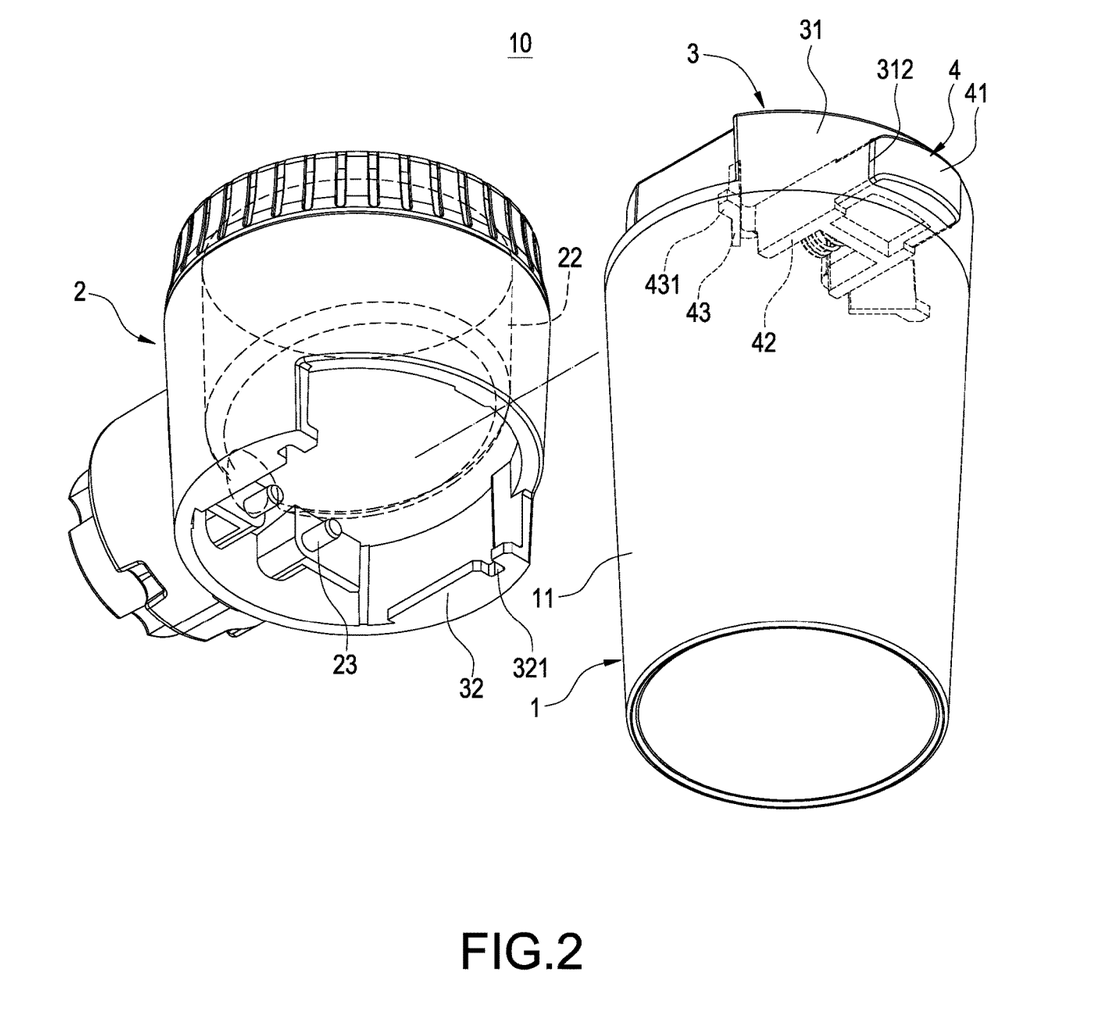
FIG. 2 is another perspective exploded view illustrating the nebulizer according to the first embodiment of the present invention.
Figure 3:
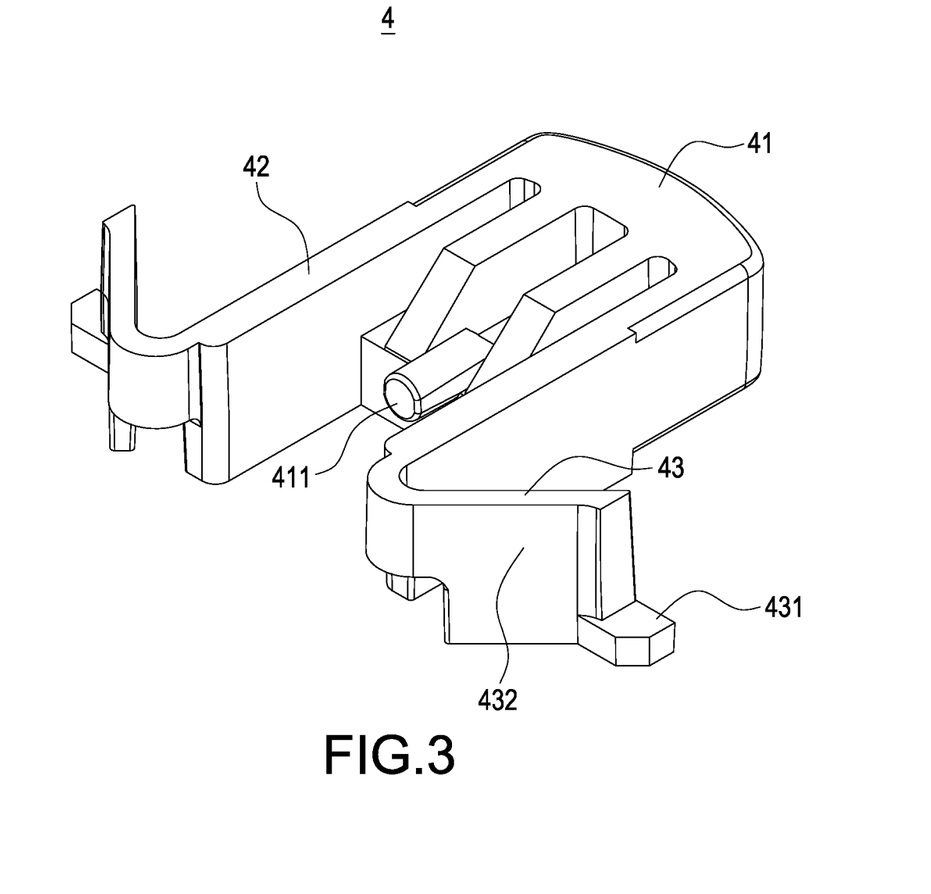
FIG. 3 is a perspective view illustrating a multi-directional resilient member of the present invention.
Figure 4:
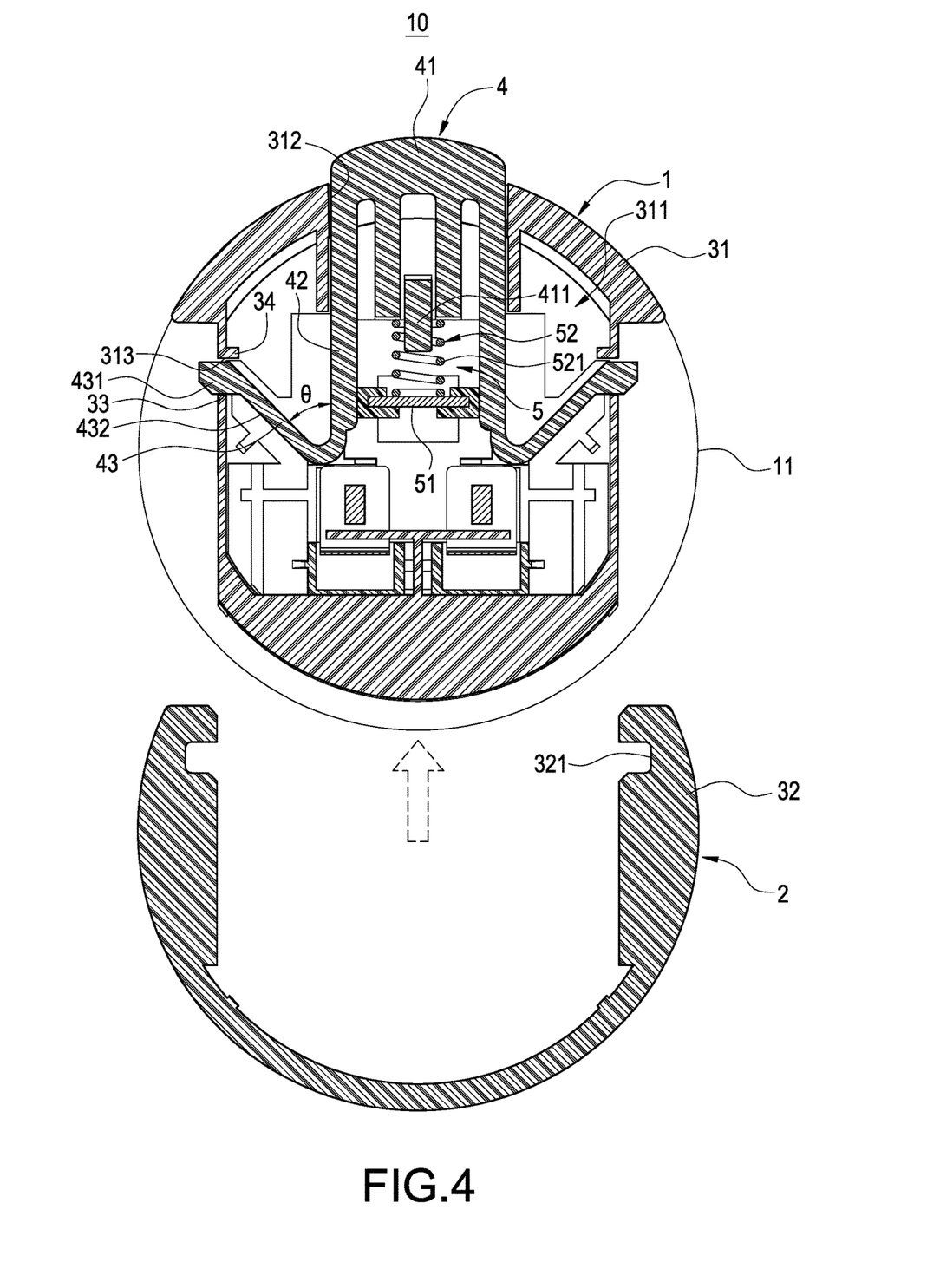
FIG. 4 is a first in-use view illustrating the nebulizer according to the first embodiment of the present invention.
Figure 5:
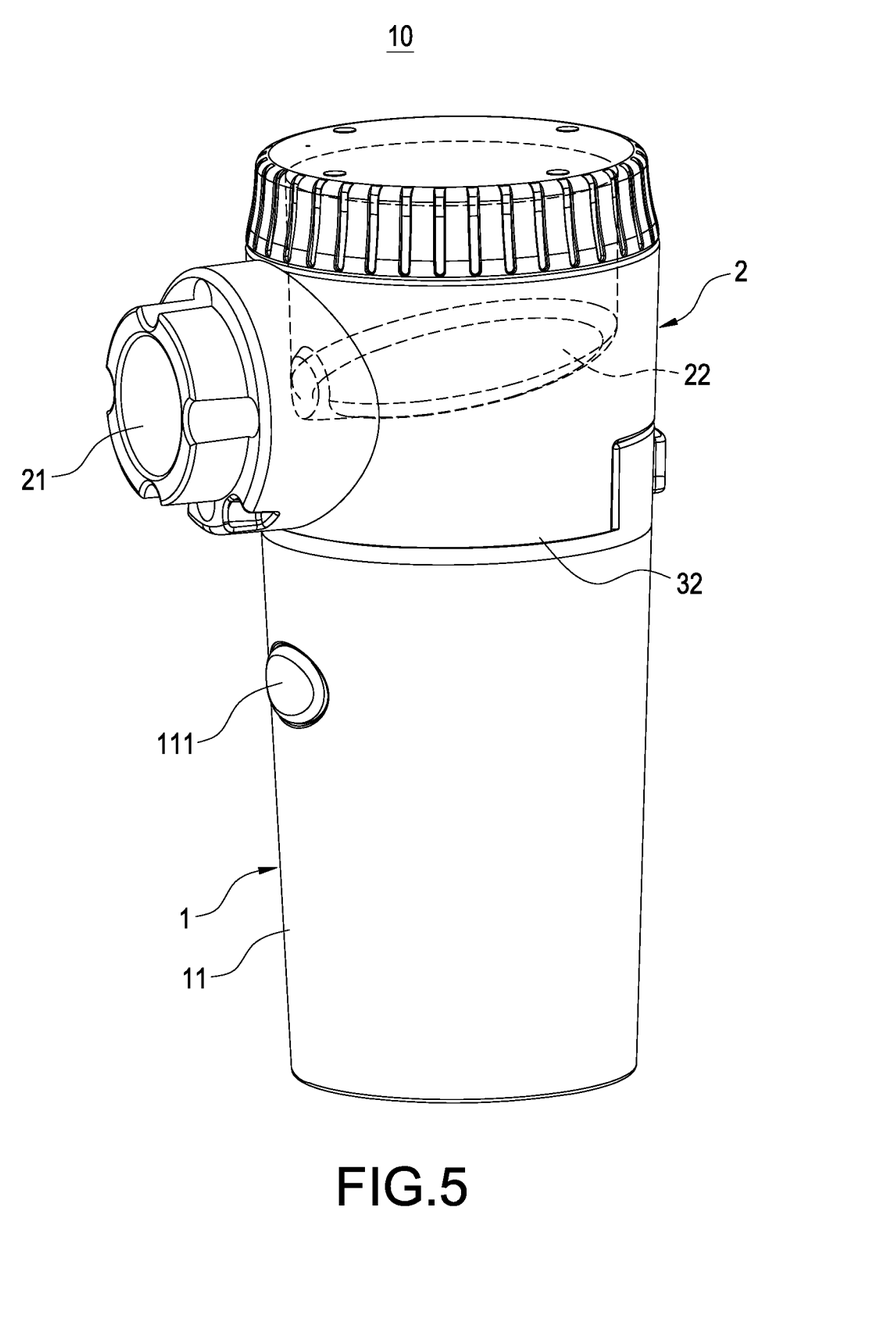
FIG. 5 is a perspective assembled view illustrating the nebulizer according to the first embodiment of the present invention.
Figure 6:
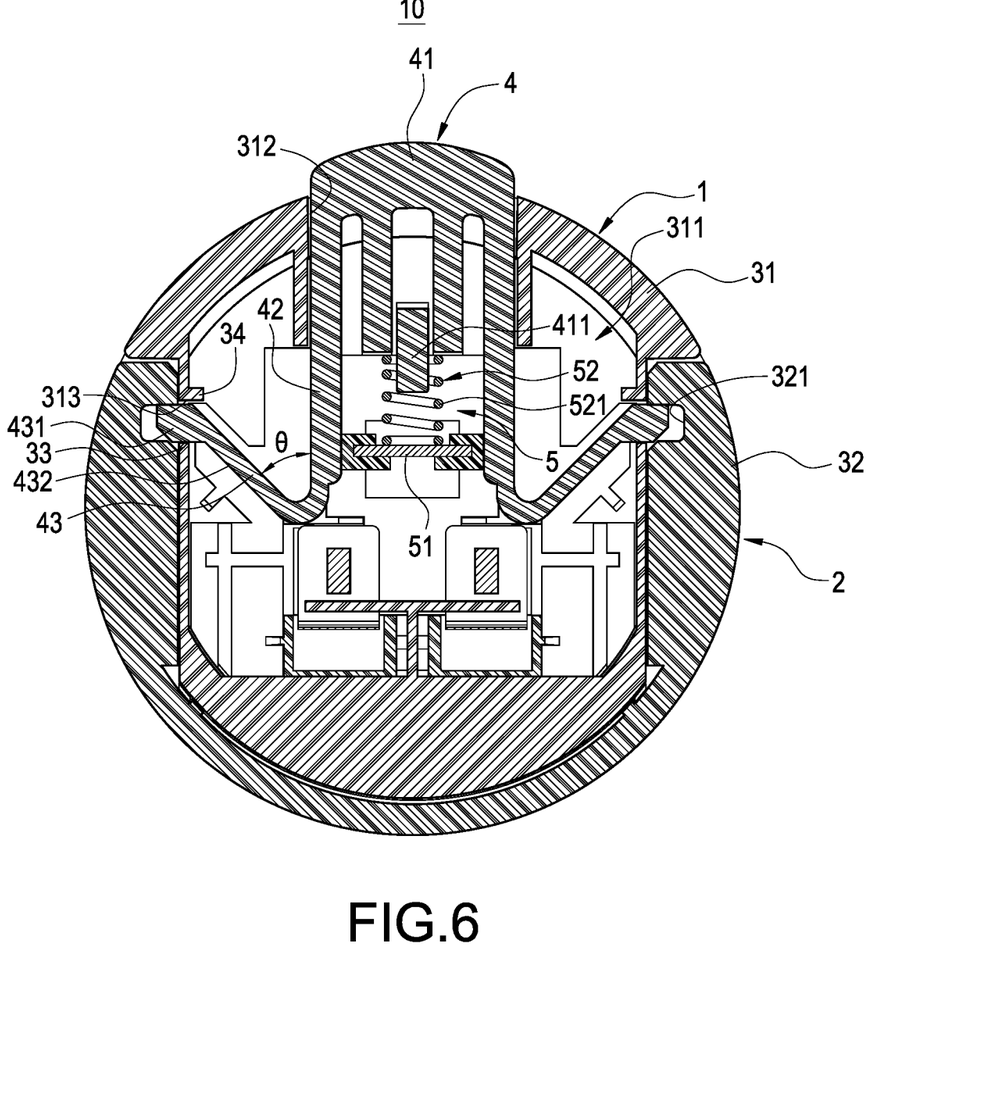
FIG. 6 is a second in-use view illustrating the nebulizer according to the first embodiment of the present invention.
Figure 7:
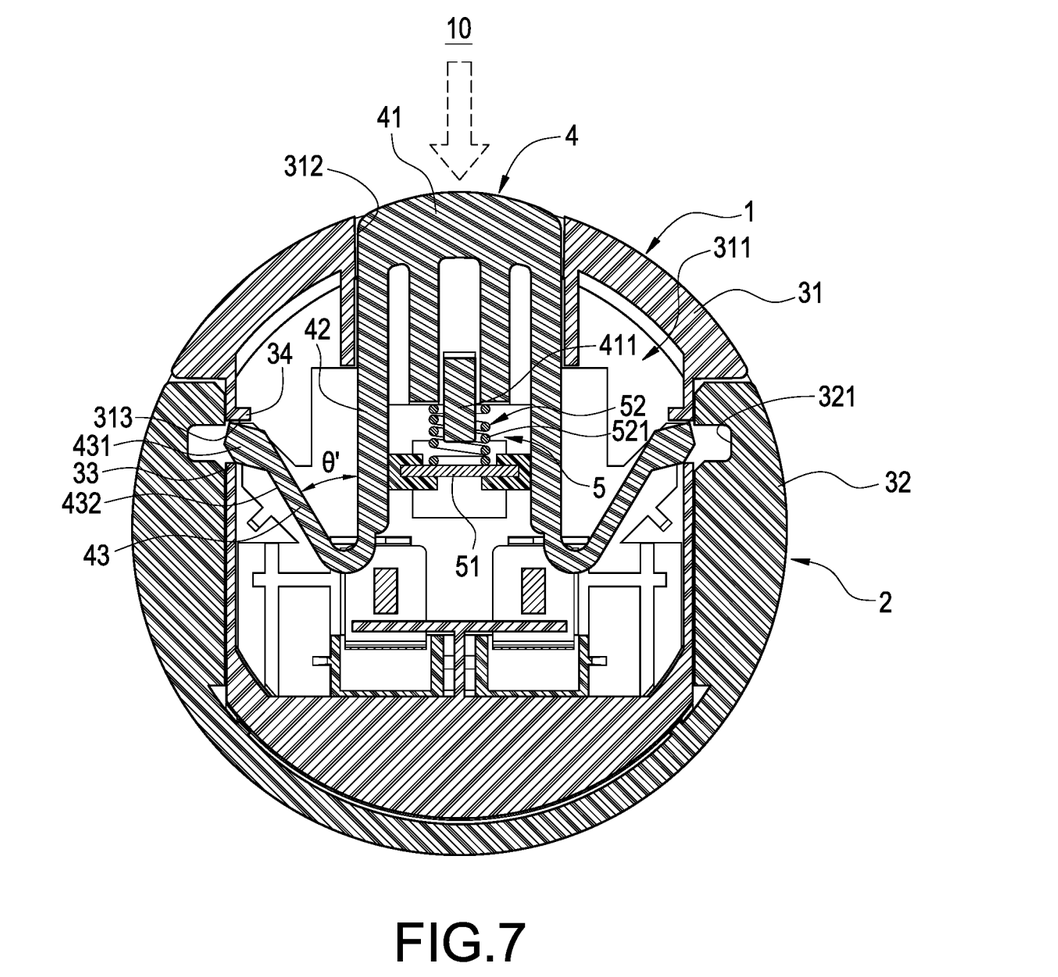
FIG. 7 is a third in-use view illustrating the nebulizer according to the first embodiment of the present invention.
Figure 8:
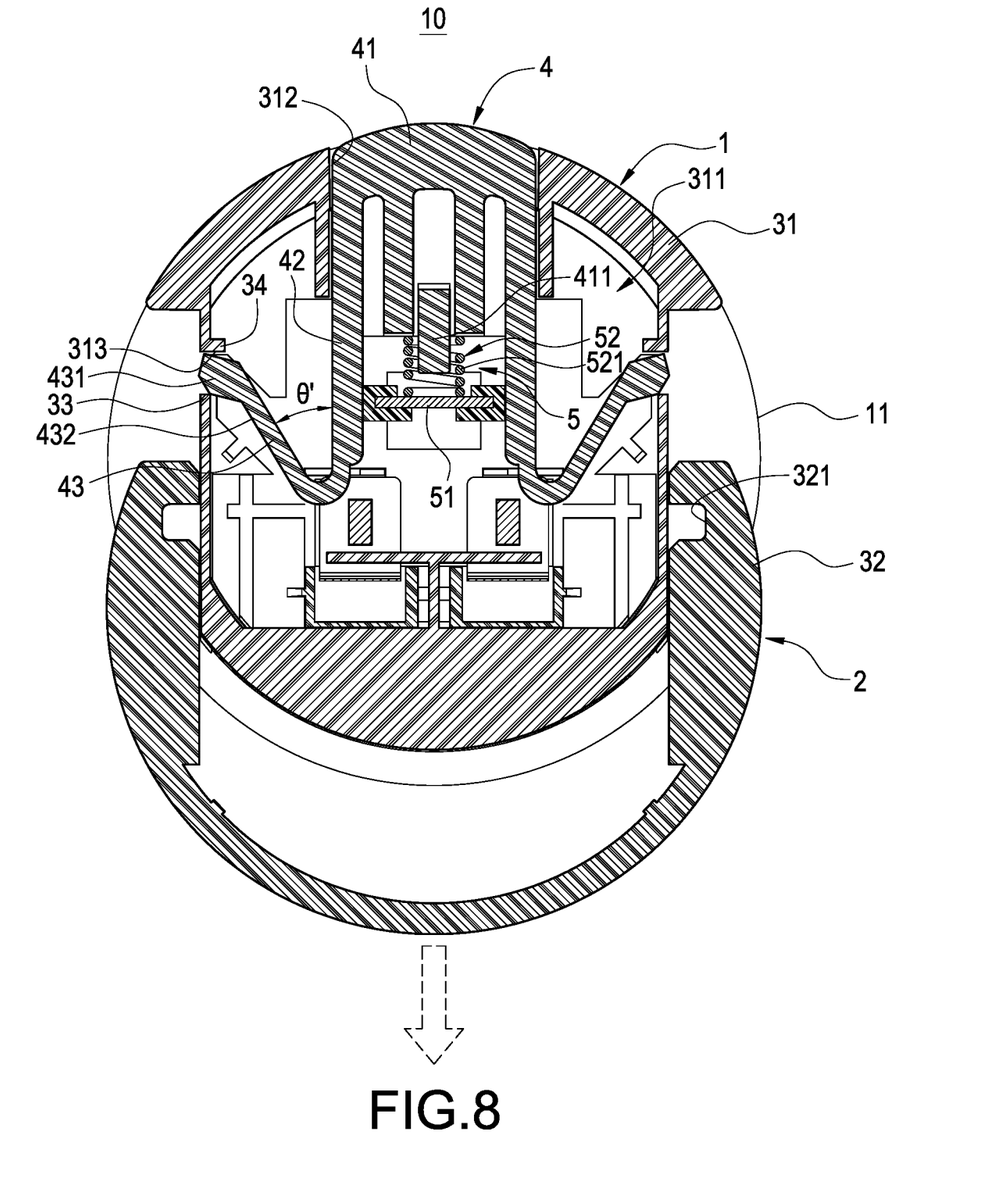
FIG. 8 is a fourth in-use view illustrating the nebulizer according to the first embodiment of the present invention.

Please refer to FIGS. 4 to 8, which are in-use views of the nebulizer 10 according to the present invention. As shown in FIGS. 4 to 6, the inner protruding base 31 is engaged with the outer protruding block 32, and the two block members 431 of the two oblique resilient arms 43 are engaged with the two engagement grooves 321 of the medicine cup 2, so that the medicine cup 2 is assembled to the body 1. As shown in FIGS. 7 and 8, when the press element 41 is pressed, the oblique resilient arm 43 is driven to move, the first blockers 33 are in contact with the respective block members 431, and thereby each of the oblique resilient arms 43 forms a second acute angle $\theta'$ with respect to a corresponding one of the straight resilient arms 42, and the second acute angle $\theta'$ is smaller than the first acute angle $\theta$ (see FIG. 6), so that the two block members 431 retract into the two through holes 313. At this point, the two block members 431 are disengaged from the two engagement grooves 321, and thus the medicine cup 2 is detached from the body 1.

As shown in FIGS. 6 to 8, each of the second blockers 34 is also in contact with each of the block members 431 to thereby restrict movement of the respective block members 431. When the press element 41 is not pressed, the multi-directional resilient member 4 is restored to its original shape, the press element 41 is exposed from the opening 312, the oblique resilient arms 43 and the straight resilient arms 42 are not squeezed, so that the second acute angle $\theta'$ between the oblique resilient arm 43 and the straight resilient arm 42 is changed back to the first acute angle $\theta$, and thereby the two block members 431 are successfully exposed from the two through holes 313.

As shown in FIG. 4 and FIGS. 4 to 8, in other embodiment of the present invention, a fixation rod 411 extends from the press element 41 and is received in the cavity 311, the nebulizer 10 further comprises a restoring assembly 5, the restoring assembly includes a clamping plate 51 and a restoring spring 52, the clamping plate 51 is disposed in the cavity 311, the restoring spring 52 is clamped between the clamping plate 51 and the press element 41. The restoring spring 52 is a helical spring 521, and the helical spring 521 receives the fixation rod 411. The restoring spring 52 is used to push the press element 41, so that the press element 41 is exposed from the opening 312. When the press element 41 is not pressed, the restoring spring 52 pushes the multi-directional resilient member 4 to restore to its original shape, so that the two block members 431 are pushed to be exposed from the two through holes 313 rapidly and smoothly when the press element 41 becomes exposed from the opening 312.

Furthermore, the multi-directional resilient element 4 includes two straight resilient arms 42 extending from the press element 41 and also includes two oblique resilient arms 43 bent backward from the two straight resilient arms 42. Therefore, when the multi-directional resilient element 4 moves, it causes movement in two different directions wherein the press element 41 is exposed from or retracts into the opening 312, and the block member 431 is exposed from or retracts into the through hole 313. By this configuration, the present invention uses the single multi-directional resilient element 4 to eliminate the need for multiple springs, and the multi-directional resilient element 4 can enable bidirectional movement for resilient restoration actions.

Figure 9:
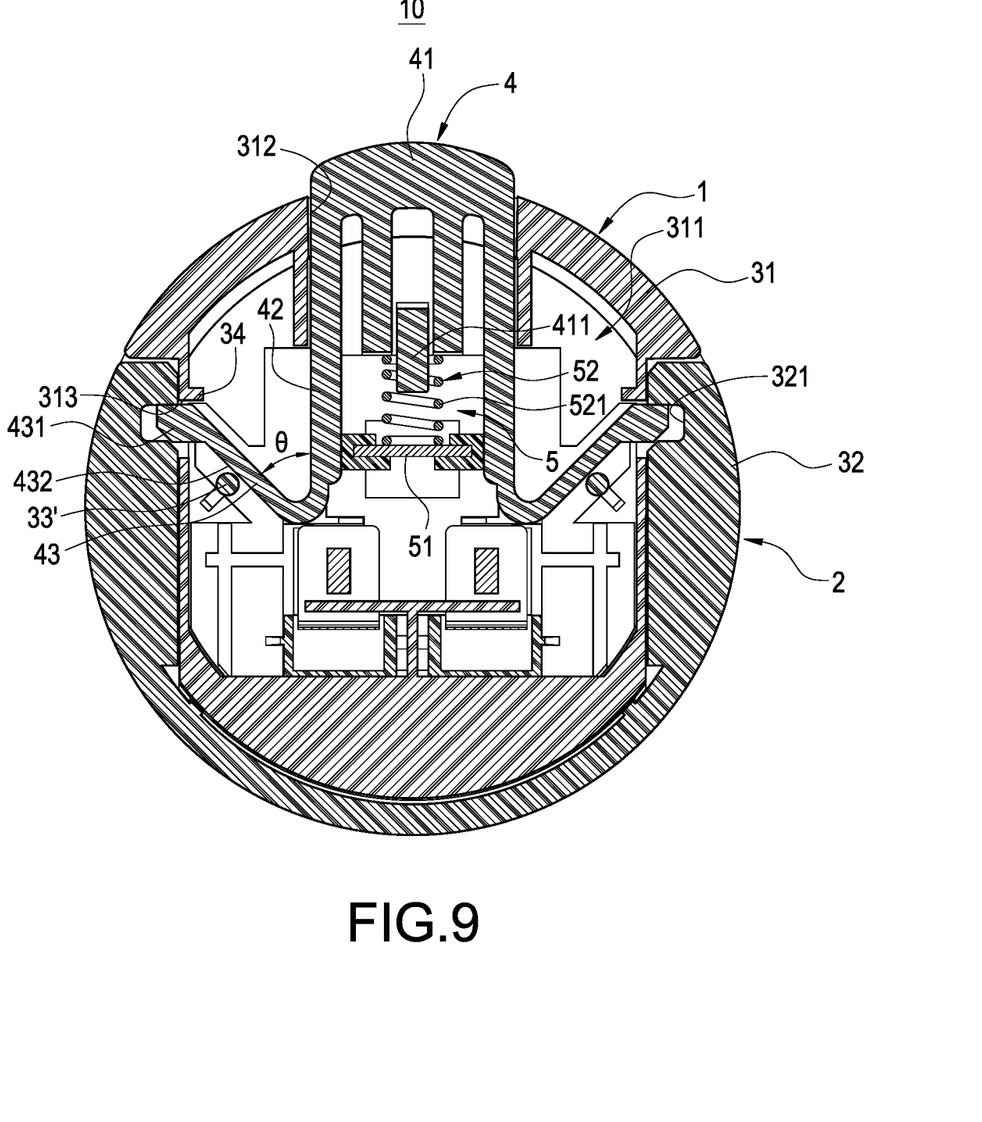
FIG. 9 is a first in-use view illustrating the nebulizer according to the second embodiment of the present invention.
Figure 10:
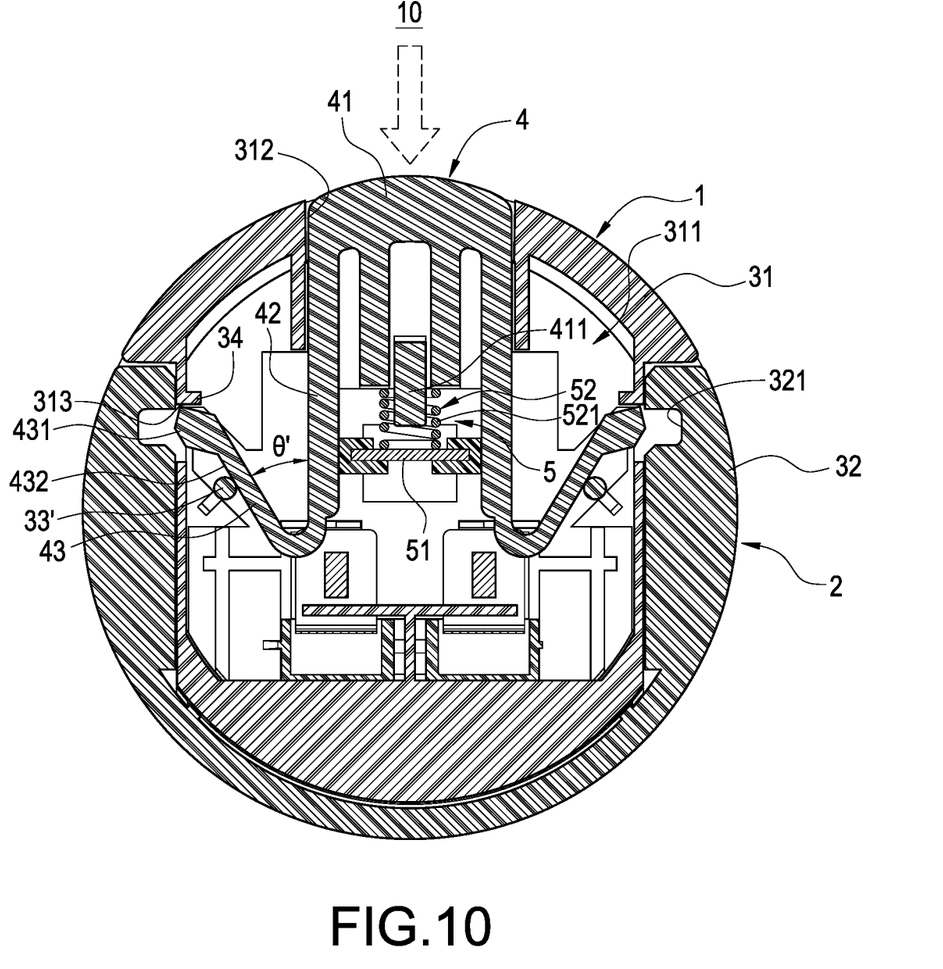
FIG. 10 is a second in-use view illustrating the nebulizer according to the second embodiment of the present invention.

Referring to FIGS. 9 and 10 showing the nebulizer 10 according to the second embodiment of the present invention, the second embodiment is substantially the same as the first embodiment, but the second embodiment is different from the first embodiment in that the first blocker 33' is disposed at a different place.

To be specific, the two first blockers 33' of the engagement structure 3 are disposed in the cavity 311 and are in contact with the respective outer oblique sides 432 of the two oblique resilient arms 43. When the press element 41 drives movement of the oblique resilient arms 43, the two first blockers 33' are in contact with the outer oblique sides 432 of the two oblique resilient arms 43, the two block members 431 retract into the two through holes 313, and the two block members 431 are thereby released from the two engagement grooves 321, so the medicine cup 2 is detached from the body 1.

It should be noted that, inside the nebulizer 10 of the present invention, the inner protruding base 31 and the outer protruding block 32 can be interchanged. To be specific, in FIGS. 1 to 8, the inner protruding base 31 extends from the body 1, and the outer protruding block 32 extends from the medicine cup 2; alternatively, the inner protruding base extends from the medicine cup 2, and the outer protruding block 32 extends from the body 1 (not illustrated).

Moreover, although the inner protruding base 31 can be extended from the medicine cup 2, and the outer protruding block 32 can be extended from the body 1, it should be noted that the inner protruding base 31 is still correspondingly engaged with the outer protruding base 32, and the multi-directional resilient member 4 is still installed in the cavity 311 (inside the inner protruding base 31), and the medicine cup 2 is assembled to or detached from the body 1 according to the same operation principle. Thus, the second embodiment achieves the same functions and effects as the first embodiment does.

It is to be understood that the above descriptions are merely the preferable embodiments of the present invention and are not intended to limit the scope of the present invention. Equivalent changes and modifications made in the spirit of the present invention are regarded as falling within the scope of the present invention.

What is claimed is:

1. A nebulizer with a press-type medicine cup, comprising:
   a body;
   a medicine cup;
   an engagement structure, the engagement structure including an inner protruding base and an outer protruding block disposed outside the inner protruding base, the inner protruding base extending from one of the body and the medicine cup, the outer protruding block extending from the other one of the body and the medicine cup, the inner protruding base including a cavity inside and including an opening and two through holes communicating with the cavity, the outer protruding block including two engagement grooves; and
   a multi-directional resilient member installed in the cavity, the multi-directional resilient member including a press element, two straight resilient arms extending from the press element, two oblique resilient arms being bent backward from the two straight resilient arms, a block member being disposed at a distal end of each of the oblique resilient arms, the press element being inserted through and exposed from the opening, the two block members being inserted through the two through holes and engaged with the two engagement grooves respectively, wherein when the press element is pressed, the two block members are driven to retract into the two through holes to be released from the two engagement grooves, so that the medicine cup is detachably connected to the body.

2. The nebulizer with the press-type medicine cup according to claim 1, further comprising a restoring assembly, the restoring assembly including a clamping plate and a restoring spring, the clamping plate being disposed in the cavity, the restoring spring being clamped between the clamping plate and the press element.

3. The nebulizer with the press-type medicine cup according to claim 2, wherein a fixation rod extends from the press element and is received in the cavity, and the restoring spring is a helical spring, and the helical spring receives the fixation rod.

4. The nebulizer with the press-type medicine cup according to claim 1, wherein the engagement structure further includes two first blockers, the two first blockers are formed at respective inner surfaces of the two through holes away from the press element, and the two first blockers are in contact with the two block members respectively.

5. The nebulizer with the press-type medicine cup according to claim 4, wherein the engagement structure further includes two second blockers, the two second blockers are formed at the respective inner surfaces of the two through holes close to the press element, and the two second blockers are in contact with the two block members respectively.

6. The nebulizer with the press-type medicine cup according to claim 1, wherein each of the oblique resilient arms includes an outer oblique side, the engagement structure further includes two first blockers, and the two first blockers are disposed in the cavity and are in contact with the respective outer oblique sides of the two oblique resilient arms.

7. The nebulizer with the press-type medicine cup according to claim 6, wherein the engagement structure further includes two second blockers, the two second blockers are formed at respective inner surfaces of the two through holes close to the press element, and the two second blockers are in contact with the two block members respectively.

8. The nebulizer with the press-type medicine cup according to claim 1, wherein when the press element is exposed from the opening, each of the oblique resilient arms forms a first acute angle with respect to a corresponding one of the straight resilient arms.

9. The nebulizer with the press-type medicine cup according to claim 8, wherein when the press element is pressed, each of the oblique resilient arms forms a second acute angle with respect to a corresponding one of the straight resilient arms, and the second acute angle is smaller than the first acute angle.

10. The nebulizer with the press-type medicine cup according to claim 1, wherein the medicine cup includes a spray hole, a medicinal liquid chamber is disposed inside the medicine cup, and the medicinal liquid chamber communicates with the spray hole.

11. The nebulizer with the press-type medicine cup according to claim 10, wherein the body is a power supply body, the power supply body includes a switch and a plurality of electrodes, the medicine cup includes a plurality of conductive portions, and each of the electrodes is electrically connected to each of the conductive portions.

* * * * *